United States Patent [19]

Taylor et al.

[11] 3,998,823
[45] Dec. 21, 1976

[54] NOVEL DERIVATIVES OF MALEOPIMARIC ACID

[75] Inventors: John Bodenham Taylor, Down Ampley; Peter John Ramm, Swindon, both of England; Ferdinand Fried, Brussels, Belgium

[73] Assignee: Roussel Uclaf, Paris, France

[22] Filed: Oct. 12, 1973

[21] Appl. No.: 405,937

[30] Foreign Application Priority Data

Oct. 13, 1972 United Kingdom ............ 47437/72

[52] U.S. Cl. .................. 260/247.2 A; 260/239 BF; 260/246 B; 260/268 PC; 260/293.61; 260/326.27; 424/250; 424/267; 424/248.54

[51] Int. Cl.² ...................................... C07D 295/00

[58] Field of Search ............ 260/247.2 A, 268 PC, 260/293.61

[56] References Cited

UNITED STATES PATENTS 3,903,300   9/1975   Shen et al. ......................... 424/317

Primary Examiner—Paul J. Killos
Attorney, Agent, or Firm—Bacon & Thomas

[57] ABSTRACT

Novel derivatives of maleopimaric acid of the formula:

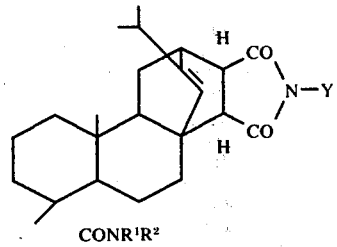

The compounds of the invention exhibit hepato-protective activity.

5 Claims, No Drawings

NOVEL DERIVATIVES OF MALEOPIMARIC ACID

This invention relates to new derivatives of maleopimaric acid showing interesting pharmacological activity.

Maleopimaric acid, which has the formula

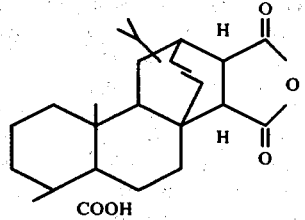

is an adduct formed between the resin acid, laevopimaric acid, and maleic anhydride. It is consequently relatively inexpensive. Although it is known to exert physiological effects in animal studies, it has not been shown to have any useful medical action.

We have now found that certain imides of maleopimaric acid show interesting hepato-protective activity. Maleopimaric acid itself does not show such activity in our tests.

According to the present invention we provide compounds of the general formula

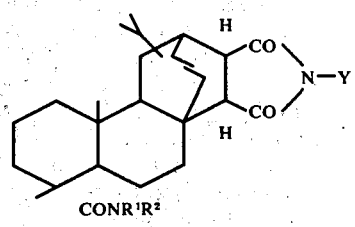

wherein $R^1$ and $R^2$ together with the intervening N represent a saturated heterocyclic group which may optionally contain one or more further heteroatoms and which may optionally carry substituents, and Y represents a hydrogen atom, an amino group, an alkyl group which may optionally carry one or more hydroxy, dialkylamino or alkoxycarbonyl groups, a acyl group or a group of the formula — $XO.CO.CO.NR^1R^2$ where $R^1$ and $R^2$ are as defined above and X represents an alkylene group, the foregoing alkyl, alkylene and acyl groups each containing up to 5 carbon atoms in all. $R^1$ and $R^2$ together with the intervening N may, for example, represent a saturated heterocyclic group having 4–6 carbon atoms in the ring, such as a morpholino, piperidino, piperazin-1-yl, pyrrolidino or hexamethyleneimino group which may carry a substituent selected from alkyl groups, hydroxyalkyl groups, phenyl groups and N-attached phenyl, alkoxycarbonyl, sulphonyl and acyl groups. Such alkyl, alkoxy or acyl groups also preferably contain up to 5 carbon atoms.

Y represents, for example, a hydroxyalkyl group or dialkylaminoalkyl group with 1 to 5 carbon atoms in each alkyl moiety.

The preferred compounds according to the invention are those of the formula I in which $R^1$ and $R^2$ together with the intervening N represent a pyrrolidino, morpholino, piperazin-1-yl, 4-lower alkyl-piperazin-1-yl or 4-hydroxy alkyl-piperazin-1-yl group; and those in which Y represents a hydrogen atom, an amino group or a β-hydroxyethyl or 3-dialkylaminopropyl, e.g. dimethylaminopropyl, group. Where Y represents a group of the formula —$CH_2CH_2O.CO.CO.NR^1R^2$, $R^1$ and $R^2$ together with the N preferably represent a morpholino, piperazin-1-yl, 4-alkyl-piperazin-1-yl, or 4-hydroxyalkyl-piperazin-1-yl group.

The nomenclature used in this specification for the imides of general formula I is the I.U.P.A.C. system based on tetradecahydrophenanthro-[1,2-c]-2',5'-pyrrolidinedione, in which formula I(a), for example, is to be regarded as

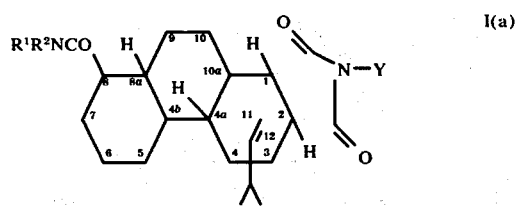

Particularly preferred compounds by virtue of their interesting hepatoprotective activity are:

1. 8β-morpholino-carbonyl-4bα,8α-dimethyl-12-isopropyl-1β,2β,3β,4,4aβ,4bβ,5,6,7,8,8aβ,9,10,10a-tetradecahydro-3,10a-ethenophenanthro[1,2-c]-1'-amino-2',5'-pyrrolidinedione;
2. 8β-morpholino-carbonyl-4bα,8α-dimethyl-12-isopropyl-1β,2β,3β,4,4aβ,4bα,5,6,7,8,8aβ,9,10,10a-tetradecahydro-3,10a-ethenophenanthro[1,2-c]-1'-(2-hydroxyethyl)-2',5'-pyrrolidinedione;
3. 8β-(4-methylpiperazin-1-yl-carbonyl)-4bα,8α-dimethyl-12-isopropyl-1β,2β,3β,4,4aβ,4bα,5,6,7,8,,8aβ,9,10,10a-tetradecahydro-3,10a-ethenophenanthro[1,2-c]-1'-amino-2',5'-pyrrolidinedione; and
4. 8β-morpholino-carbonyl-4bα,8α-dimethyl-12-isopropyl-1β,2β,3β,4,4aβ,4bα,5,6,7,8,8aβ,9,10,10a-tetradecahydro-3,10a-ethenophenanthro[1,2-c]-1'-(3,3-dimethylaminopropyl)-2',5'-pyrrolidinedione.

The compounds of the present invention show interesting pharmacological activity, in particular hepatoprotective activity. The following pharmacology shows the activity found for the compounds 1 to 4 listed above.

The hepatoprotective activity has been evaluated relative to hepatitis caused by intraperitoneal injection of galactosamine in the rat according to the technique of D. Keppler, et. al. (1968) Exptl. & Mo. Path. 9, October 2nd, pp 279 to 290 as follows:

Male rats weighing about 180 g were divided up into three batches each of ten animals. The first batch of animals received intraperitoneally 1 ml/kg of a 0.9% sodium chloride solution in distilled water, on each of 5 consecutive days. The second batch of animals received intraperitoneally 400 mg/kg of galactosamine dissolved in 0.9% sodium chloride solution, on the third day at zero hour, the eighth hour and the twenty-fourth hour. The third batch of animals received the same dosage of galactosamine as the second batch and at the same times, but also received the product under test as an oral dose of 250 mg/kg in aqueous suspension on each of the 5 consecutive days.

On the fifth day the blood of the animals of all three batches (treated batch and control batches) was removed and for each batch the average serum concentration of glutamic-oxaloacetic transaminases (S.G.O.T), and glutamic-pyruvic transaminases (S.G.P.T.), was determined.

The results obtained were as follows:

TABLE 1

| | Animals treated by: | S.G.O.T. units/l | S.G.P.T. units/l |
|---|---|---|---|
| Batch 1 | Sodium chloride, 5 days, intraperitoneally | 87 | 26 |
| Batch 2 | galactosamine 400 mg/kg intraperitoneally, Day 3, at 0, 8 and 24 hours | 2134 | 575 |
| Batch 3 | galactosamine 400 mg/kg intraperitoneally, Day 3, at O, 8 and 24 hours; Compound 1, 250 mg/kg orally, 5 days | 253 | 45 |

TABLE 2

| | Animals treated by: | S.G.O.T. units/l | S.G.P.T. units/l |
|---|---|---|---|
| Batch 1 | Sodium chloride, 5 days, intraperitoneally | 66 | 29 |
| Batch 2 | galactosamine 400 mg/kg intraperitoneally, Day 3, at O, 8 and 24 hours | 3849 | 3133 |
| Batch 3 | galactosamine 400 mg/kg intraperitoneally, Day 3, at O, 8 and 24 hours; Compound 2, 250 mg/kg orally, 5 days | 340 | 125 |

TABLE 3

| | Animals treated by: | S.G.O.T. units/l | S.G.P.T. units/l |
|---|---|---|---|
| Batch 1 | Sodium chloride, 5 days, intraperitoneally | 82 | 33.8 |
| Batch 2 | galactosamine 400 mg/kg intraperitoneally, Day 3, at O, 8 and 24 hours | 2000 | 606.8 |
| Batch 3 | galactosamine 400 mg/kg intraperitoneally, Day 3, at O, 8 and 24 hours; Compound 3, 250 mg/kg orally, 5 days | 311.3 | 111.6 |

TABLE 4

| | Animals treated by: | S.G.O.T. units/l | S.G.P.T. units/l |
|---|---|---|---|
| Batch 1 | Sodium chloride, 5 days, intraperitoneally | 52.3 | 49.8 |
| Batch 2 | galactosamine 400 mg/kg intraperitoneally, Day 3, at O, 8 and 24 hours | 1748 | 786 |
| Batch 3 | galactosamine 400 mg/kg intraperitoneally, Day 3, at O, 8 and 24 hours; Compound 4, 250 mg/kg orally, 5 days | 146 | 80.9 |

The results clearly show that the average serum concentration of glutamic-oxaloacetic transaminases and glutamic-pyruvic transaminases is markedly reduced by administration of the test products.

Finally it was observed that the test compounds were almost non-toxic. Thus, for example, the administration by the oral route to a batch of 10 mice of 6000 mg/kg of Compound 1 did not cause the death of any animal. In the same way the administration of this product by the oral route to a batch of 10 rats at a dose of 5000 mg/kg did not cause the death of any animal.

According to a further feature of the present invention therefore, we provide pharmaceutical compositions containing a compound of the formula I as defined above together with a pharmaceutical carrier or excipient. These compositions are of use in the treatment of inter alia chronic hepatitis. The compositions may be administered by the oral, parenteral or rectal routes. The compositions may thus be solid or liquid and may take the usual forms of tablets, coated tablets, capsules, solutions, syrups, suppositories and parenteral preparations such as injection ampoules. The carriers and excipients used may include the conventional ingredients, for example, talc, gum arabic, lactose, starch, magnesium stearate, cocoa butter, sterile aqueous or non-aqueous vehicles, animal or vegetable fatty substances, paraffin derivatives, glycols, wetting, dispersing and emulsifying agents and preservatives.

The compositions are desirably presented in dosage unit form, each unit containing 25 mg to 500 mg of compound of the compound of the formula I, advantageously 50 mg to 250 mg. The oral daily dose in humans is generally 25 mg to 1000 mg, advantageously 250 mg to 500 mg depending of course on the nature of the illness and the particular patient.

The compounds according to the invention may be prepared by any convenient method. In particular they may be prepared by subjecting maleopimaric acid to the steps of:

a. reaction with a reagent of the formula $H_2NY$ where Y is as defined for formula I whereby the anhydride grouping is converted into the required imido grouping;

b. reaction, in the form of a reactive amide-forminng derivative thereof or in the presence of a dehydrating agent, with a reagent of the formula $HNR^1R^2$ whereby the carbonyl group is converted into $CONR^1R^2$; the steps (a) and (b) being effected in either order with the exception that where Y represents an $-NH_2$ group, reaction (b) is preferably effected first; and, where the product from step (a) is a compound of formula I in which Y represents a hydrogen atom and a final product is required in which Y represents an alkyl or acyl group;

c. subsequent reaction of a salt of the imide with a reagent YA, where Y represents an alkyl or acyl group as defined for formula I and A represents a radical which can be eliminated in the form of an anion, step (c) being effected at any stage after step (a).

The imide-forming reaction may be effected either in the presence or absence of a solvent for the maleopimaric derivative, the reagent $H_2NY$ itself conveniently forming the reaction medium in many cases. An inert solvent such as an ether or a lower alcohol, e.g. dioxan or methanol may however be present. Ammonia may, for example be reacted in aqueous solution, the maleopimaric acid or amide being in suspension therein.

The amide-forming reaction using maleopimaic acid itself requires suitable dehydrating conditions, for example, the use of dicyclohexyldiimide. Conveniently, however, an acid halide may be used as a reactive derivative, preferably the chloride. The reaction in this case may conveniently be effected in an inert solvent such as dry benzene preferably using a small excess of the compound of formula $NHR^1R^2$.

The acid halide may be prepared from the free carboxylic acid using a conventional halogenating agent e.g. thionyl chloride, a phosphorus halide, such as phosphorus trichloride or phosphorus pentachloride, or an oxalyl halide. In particular the chloride may be prepared by treatment with oxalyl chloride.

Step (c), the reaction with a reagent YA, requires a salt of the unsubstituted imide of formula I in which Y is hydrogen. Conveniently, an alkali metal salt, especially the potassium salt may be used and this may be prepared by reaction of the unsubstituted imide with an appropriate base, e.g. an alkali metal hydroxide, especially potassium hydroxide. The radical A of the reagent YA comprises a radical which can be eliminated in the form of an anion and is preferably a halogen, e.g. a bromide, iodide or chloride atom, or a p-toluene sulphonyloxy or methane sulphonyloxy group. Examples of the reagent YA include haloesters, e.g. ethyl bromoacetate; acylhalides, e.g. acetyl chloride; alkyl halides, e.g. methyl iodide and ethyl bromide; and hydroxyalkyl halides, e.g. 3-chloropropan-1-ol. The reaction is preferably effected in an inert solvent, e.g. an amide solvent such as dimethylformamide.

The compounds of the formula I in which Y represents a group —XO.CO.CO.NR$^1$R$^2$ where R$^1$ and R$^2$ have the same significance as they have in the amide group at the 8β-position are conveniently prepared by effecting step (a) using an ω-hydroxyalkylamine and then step (b) using at least 2 moles of the reagent HNR$^1$R$^2$, but first using an oxalyl halide, especially the chloride, in the preparation of the acid halide. In this way the oxalyl halide half-ester of the hydroxyalkyl group is formed and also reacts with the reagent HNR$^1$R$^2$.

The following examples illustrate the invention further (all temperatures are in °C).

PREPARATION OF STARTING MATERIALS a. Maleopimaric acid chloride — using oxalyl chloride Maleopimaric acid (30 g) was dissolved in sodium dry benzene (ca 600 ml) distilled directly into the vessel. This solution was then distilled at atmospheric pressure until about 200 ml of distillate had been collected. The remaining solution, suitably protected from atmospheric moisture, was cooled to 10° and oxalyl chloride (15 ml; 22 g) was added with stirring over a period of 1 hour. The reaction mixture was allowed to warm to room temperature and stirring continued for a further 2 hours after which no further evolution of gas was observed. The solution was evaporated to dryness under vacuum giving crude maleopimaric acid chloride. Dry benzene (ca 300 ml) was distilled directly into the vessel containing the crude acid chloride and the resulting solution used.

b. Maleopimaric acid chloride — using thionyl chloride

Maleopimaric acid (80 g; 0.2 mole) was dissolved in benzene (ca 800 ml) with warming and the resulting solution azeotroped until no more water was present in the distillate (ca 150 ml of distillate). To this solution was added dimethylformamide (1.5 ml. 0.02 mole). The solution was then stirred during the dropwise addition of thionyl chloride (26.2 g; 16.0 ml; 0.22 mole) over a period of one hour. Stirring was continued overnight. The resulting solution of the acid chloride was normally used directly without further purification. A small sample was purified by evaporating to dryness and recrystallising from dichloromethane:ether and gave the acid chloride m.p. 188°–190°.

c.
8β-Morpholino-carbonyl-4bα,8α-dimethyl-12-isopropyl-1β,
2β,3β,4,4aβ,,4bα,5,6,7,8,8aβ,9,10,10a-tetradecahydro-3,10a-ethenophenanthrene(maleopimaryl morpholide)

The acid chloride solution from (b) above was added over a period of 2 hours to a stirred solution of morpholine (19 g; 19 ml; 0.22 mole) and triethylamine (40 g; 55 ml; 0.4 mole) in dry benzene (ca 200 ml) cooled in an ice bath. After the addition was complete, cooling was removed and the reaction mixture allowed to warm to room temperature, stirring being continued for a further 16 hours. The reaction mixture was concentrated by evaporation in vacuo and the residues partitioned between dichloromethane and dilute hydrochloric acid. The organic extract was separated and washed first with dilute sodium bicarbonate solution and then twice with water. After being dried (MgSO$_4$), the solution was evaporated yielding a crystalline product, which was recrystallized from dichloromethane:ether to give maleopimaryl morpholide (62.1 g) as rhombic plates; m.p. 171°–173°.

EXAMPLE 1

8β-Morpholinocarbonyl-4bα,8α-dimethyl-12-isopropyl-1β,2β,3β,4,4aβ,4bα,5,6,7,8,8aβ,9,10,10a-tetradecahydro-3,10a-ethenophenanthro[1,2-c]-2',5'-pyrrolidinedione (maleopimarimidyl morpholide)

A slurry of maleopimaric acid (50 g.) in 0.880 (density) ammonia solution (250 mls.) was heated slowly. At about 70° all the solid had dissolved and when the temperature reached 100° (after approx. 1 hour) the excess of ammonia was boiled off. The remaining material was then heated to 170° over a period of 1½ hours. After cooling the residual solid was dissolved in dioxan and a few drops of 5 N hydrochloric acid added. Addition of a large volume of water resulted in the deposition of a tan coloured product. This was recrystallized from aqueous ethanol giving 26.5 g. of maleopimarimide, as colourless crystals, m.p. 275°–280° (decomp.)

Maleopimarimide (24 g.) was suspended in dry benzene (250 ml.) and stirred at room temperature while oxalyl chloride (23 g; 15 ml; 3 × excess) was added dropwise over a period of 30 minutes. Stirring was continued for a further 3 hours by which time evolution of gas had ceased. Evaporation of the clear solution left maleopimarimide acid chloride as a white solid.

The acid chloride (8 g) without further purification was dissolved in dry benzene (100 ml.) and the resulting solution cooled (10°) and stirred while morpholine (3.5 g; 3.5 ml; 2 mole equiv.) was added dropwise over a period of 30 minutes. The reaction mixture was allowed to warm to room temperature and stirring was continued overnight before the solvent was removed in vacuo. The white residue was partitioned between chloroform and water. After separation, the organic layer was washed once more with water and then dried over magnesium sulphate. Evaporation of the solvent gave a crude white product which was crystallised from benzene:petrol to give colourless crystals of maleopimarimide morpholide (7.6 g.); m.p. 160°–162° (decomp).

EXAMPLE 2

8β-Morpholinocarbonyl-4bα,8α-dimethyl-12-isopropyl-1β,2β,3β,4,4aβ,4bα,5,6,7,8,8aβ,9,10,10a-tetradecahydro-3,10a-ethenophenanthro[1,2-c]-1'-(amino)-2',5'-pyrrolidinedione
(N-aminomaleopimarimidyl morpholide)

Maleopimaryl morpholide (10 g; 0.021 mole) suspended in dioxan (60 ml) was added dropwise to a stirred solution of hydrazine hydrate (20 g; 0.42 mole) in dioxan at 10°–15°. The resulting mixture was stood overnight at room temperature before 5 N hydrochloric acid was added to bring the pH to 3. Addition of a large excess of water resulted in the deposition of a crystalline product. Recrystallisation of the filtered material from aqueous ethanol gave N-aminomaleopimarimidyl morpholide (7.2 g); m.pt. 198°–200°;

EXAMPLE 3

8β-Morpholinocarbonyl-4bα,8α-dimethyl-12-isopropyl-1β,2β,3β,4,4aβ,4bα,5,6,7,8,8aβ,9,10,10a-tetradecahydro-3,10a-ethenophenanthro[1,2-c]-1'-(2-hydroxyethyl)-2',5'-pyrrolidinedione To a solution of maleopimaryl morpholide (10 g, 0.021 mole) in methanol (150 ml), ethanolamine (1.8 g; 0.03 mole) was added and the resulting solution was refluxed for 3 hours. The volume of the solution was reduced to ca 100 ml. by evaporation in vacuo and the resulting solution deposited crystals on cooling. Recrystallisation from aqueous methanol gave the hydroxyethyl imide (7.5 g) m.pt. 195°–199°.

EXAMPLE 4

8β-Morpholinocarbonyl-4bα,8α-dimethyl-12-isopropyl-1β,2β,3β,4,4aβ,4bα,5,6,7,8,8aβ,9,10,10a-tetradecahydro-3,10a-ethenophenanthro[1,2-c]-1'-(5-morpholino-3-oxo-4,5-dioxopentyl)-2',5'-pyrrolidinedione 2-Aminoethanol (3.10 g) was added to maleopimaric acid (10 g.) dissolved in methanol (100 ml) and the resulting solution was refluxed for 18 hours. The reaction mixture was evaporated to dryness leaving a gum which was subsequently crystallised. Recrystallisation from methanol:water gave 7.8 g of N-(2-hydroxyethyl)-maleopimarimide m.pt. 227°–229°.

To a stirred suspension of this intermediate (5 g) in dry benzene (50 ml) was added oxalyl chloride (5.7 ml; 8.5 g) over a period of 30 minutes. After 2 hours, when no further evolution of gas was observed, the excess oxalyl chloride and the solvent were removed by evaporation in vacuo. The residue was dissolved in dry benzene (100 ml) and cooled to 10°, while morpholine (4 ml; 4 g) was added dropwise with stirring during a period of one hour. The reaction mixture was allowed to warm to room temperature, stirring being continued for 15 hours. Evaporation of the solvent left a semisolid which was partitioned between chloroform and dilute hydrochloric acid. The chloroform layer was separated and washed first with sodium bicarbonate solution and then with water (× 2). Drying of the solution (MgSO$_4$) was followed by evaporation of the solvent to leave a pale yellow gum which was crystallised from dichloromethane:ether giving the named product (3.2 g); m.pt. 154°–159°.

EXAMPLE 5

8β-Morpholinocarbonyl-4bα,8α-dimethyl-12-isopropyl-1β,2β,3β,4,4aβ,4bα,5,6,7,8,8aβ,9,10,10a-tetradecahydro-3,10a-ethenophenanthro[1,2-c]-1'-(3-dimethylaminopropyl)-2',5'-pyrrolidinedione 3-Dimethylaminopropylamine (2.7 g; 0.026 mole) was added to maleopimaryl morpholide (10 g; 0.021 mole) dissolved in dry benzene (150 ml) and the resulting solution heated under reflux using a Dean-Stark apparatus. Heating was continued for four hours although separation of water was complete after 1 hour. On cooling a crystalline mass separated, and this was collected and recrystallised from aqueous ethanol to give the 3-dimethylaminopropylimide (7.0 g), m.pt. 70°–74°.

EXAMPLE 6

8β-[4-(2-hydroxyethyl)-piperazin-1-ylcarbonyl]-4bα,8α-dimethyl-12-isopropyl-1β,2β,3β,4,4aβ,4bα,5,6,7,8,,8aβ,9,10,10a-tetradecahydro-3,10a-ethenophenanthro[1,2-c]-1'-(2-hydroxyethyl)-2',5'-pyrrolidinedione Maleopimaric acid chloride [prepared from 20 g. of maleopimaric acid] was dissolved in dry benzene (150 ml) and added to a cooled (10°), stirred solution of N'-(2-hydroxyethyl)piperazine (7.2 g; 1.1 mole equiv.) and triethylamine (5 g; 1 mole equiv.) in dry benzene (200 ml). The reaction mixture was allowed to warm to room temperature and stirring was continued overnight. The solvent was removed in vacuo and the solid residue partitioned between chloroform and dilute hydrochloric acid. After separation the organic extract was washed with sodium bicarbonate solution and water before being dried (MgSO$_4$). Evaporation of the solvent gave a pale yellow gum. Maleopimaric acid -4'-(2-hydroxyethyl)-piperazide (13.8 g) was precipitated by addition of ether to a dichloromethane solution of the crude product. The amide showed i.r. 3450 (—OH), 2970, 2940 ($\geqslant$CH), 1845, 1780 (—CO-O-CO—) and 1630 cm$^{-1}$ (-CO-N<).

The amide (10.2 g.) was dissolved in methanol (150 ml.) and ethanolamine (1.46 g; 1.2 mole equiv.) added. The solution was heated under reflux for 3 hours. Evaporation of the solvent left a white residue which was crystallised from aqueous methanol giving 4.1 g of the N-hydroxyethyl imide; m.p. 148°–50°.

EXAMPLE 7

8β-Morpholinocarbonyl-4bα,8α-dimethyl-12-isopropyl-1β,2β,3β,4,4aβ,4bα,5,6,7,8,8aβ,9,10,10a-tetradecahydro-3,10a-ethenophenanthro[1,2-c]-1'-(ethoxycarbonylmethyl)-2',5'-pyrrolidinedione A solution of potassium hydroxide (3.6g; 0.064 mole) in ethanol:water; 4:1 (50 ml) was added to a suspension of maleopimarimidyl morpholide (30g; 0.064 mole) in ethanol (100 ml). The mixture was stirred at room temperature until it became clear (ca 0.5 hrs). After evaporation of the mixture to dryness under reduced pressure (adding more ethanol in order to remove all water present) a white glass-like solid, the potassium salt of maleopimarimidyl morpholide, remained; m.p. 242°–246°.

The salt was recrystallised only with difficulty and therefore was used without further purification.

Ethyl bromoacetate (2.65 ml; 4.0 g; 0.25 mole) was added dropwise to a stirred solution of the potassium salt of maleopimarimidyl morpholide (10 g; 0.02 mole) in dimethylformamide (50 ml). Stirring was continued for 1 hour after the addition was complete and then water (150 ml) was added. The resulting precipitated solid was filtered off and crystallised from methanol:-water to give the N-(ethoxycarbonylmethyl)-imide (7.9 g) m.p. 126°–127°.

The following Examples 8 to 19 illustrate the preparation of further compounds according to the present invention. They are presented in table form with reference to the earlier examples for description of the method used.

$8\beta$-morpholino-carbonyl-$4b\alpha,8\alpha$-dimethyl-12-isopropyl-$1\beta,2\beta,3\beta,4,4a\beta,4b\alpha,5,6,7,8,8a\beta,9,10.10$a-tetradecahydro-3,10a-ethenophenanthro[1,2-c]-1'-(2-hydroxy-ethyl)-2',5'-pyrrolidinedione: 150 mg.
Aqueous solvent: q.s. for 2 cm$^3$.

What is claimed is:
1. A compound of the general formula:

| EXAMPLE | NR$^1$R$^2$ | Y | Melting point (° C) | MOLECULAR FORMULA | Prepared by method analogous to Example | Reagents |
|---|---|---|---|---|---|---|
| 8 | 4-methyl-piperazin-1-yl | H | 257–263 | C$_{29}$H$_{43}$N$_3$O$_3$ | 1 | Maleopimarimide oxalyl chloride N-methylpiperazine |
| 9 | 4-methyl-piperazin-1-yl | NH$_2$ | 223.5–226 | C$_{29}$H$_{44}$N$_4$O$_3$ | 2 | Maleopimaryl 4-methylpiperazide hydrazine |
| 10 | piperazin-1-yl | H | | C$_{28}$H$_{41}$N$_3$O$_3$ | 1 | Maleopimarimide oxalyl chloride piperazine |
| 11 | pyrrolidino | NH$_2$ | 88–91 | C$_{28}$H$_{41}$N$_3$O$_3$ | 2 | maleopimaryl-pyrrolidide hydrazine |
| 12 | pyrrolidino | H | 148–153 | C$_{28}$H$_{40}$N$_2$O$_3$ | 1 | maleopimarimide oxalyl chloride pyrrolidine |
| 13 | 4-methyl-piperazin-1-yl | 217-1-yl)-3-oxa-4,5-dioxopentyl | 223 | C$_{36}$H$_{57}$N$_5$O$_6$ | 4 | maleopimaric acid ethanolamine oxalyl chloride N-methylpiperazine |
| 14 | piperazin-1-yl | 5-piperazin-1-yl-3-oxa-4,5-dioxopentyl | 212–220 | C$_{36}$H$_{53}$N$_5$O$_6$ | 4 | maleopimaric acid ethenolamine oxalyl chloride piperazine |
| 15 | 4-methyl-piperazin-1-yl | 3-dimethylaminopropyl | 155–158 | C$_{33}$H$_{54}$N$_4$O$_3$ | 5 | maleopimaryl-4-methylpiperazide 3-dimethylamino-propylamine |
| 16 | Morpholino | —CH$_3$ | 123–124° | C$_{29}$H$_{42}$N$_2$O$_4$ | 7 | Potassium maleopimarimidyl morpholide methyl iodide |
| 17 | Morpholino | —CH$_2$CH$_3$ | 221–223° | C$_{30}$H$_{44}$N$_2$O$_4$ | 7 | Potassium maleopimarimidyl morpholide ethyl bromide |
| 18 | Morpholino | —COCH$_3$ | 186–188° | C$_{30}$H$_{42}$N$_2$O$_5$ | 7 | Potassium maleopimarimidyl morpholide acetyl chloride |
| 19 | Morpholino | —(CH$_2$)$_3$OH | 179–180° | C$_{31}$H$_{46}$N$_2$O$_5$ | 7 | Potassium maleopimarimidyl morpholide 3-chloropropan-1-ol |

Examples of pharmaceutical preparations 1.
Compressed tablets of the formula:

$8\beta$-(4-methylpiperazin-1-yl-carbonyl)-$4b\alpha,8\alpha$-dimethyl-12-isopropyl-$1\beta,2\beta,3\beta, 4,4a\beta,4b\alpha,5,6,7,8,8a\beta,9,10,10$a-tetradecahydro-3,10a-ethenophenanthro[1,2-c]-1'-amino-2',5'-pyrrolidinedione: 200 mg.

Excipient: q.s. for a compressed tablet. The tablets are prepared with typical excipients, e.g., lactose, starch, talc, magnesium stearate.

2. Compressed tablets of the formula:
$8\beta$-morpholino-carbonyl-$4b\alpha,8\alpha$-dimethyl-12-isopropyl-$1\beta,2\beta,3\beta,4,4a\beta,4b\alpha,5,6,7,8,8a\beta,9,10,10$a-tetradecahydro-3,10a-ethenophenanthro[1,2-c]-1'-(2-hydroxy-ethyl)-2',5'-pyrrolidinedione: 200 mg.

Excipient: q.s. for a compressed tablet. The tablets are prepared with typical excipients, e.g., lactose, starch, talc, magnesium stearate.

3. Injectable solution of the formula:

wherein R$_1$ and R$_2$ together with the intervening nitrogen form a saturated six member heterocyclic ring which may be interrupted by another nitrogen or an oxygen and may be substituted by a lower alkyl, or hydroxy lower alkyl; Y is a hydroxy lower alkyl.

2. The compound of claim 1 in which R$^1$ and R$^2$ together with the intervening N represent a morpholino, piperidino, piperazin-1-yl group.

3. The compound of claim 1 in which R$^1$ and R$^2$ together with the intervening N represent morpholino, piperazin-1-yl, 4-lower alkyl-piperazin-1-yl or 4-hydroxyalkylpiperazin-1-yl group.

4. The compound of claim 1 selected from the group consisting of 8β-morpholino-carbonyl-4βα,8α-dimethyl-12-isopropyl-1β,2β,3β,4,4aβ,4bα,5,6,7,8,8aβ,9,10,10a-tetradecahydro-3,10a-ethenophenanthro[1,2-c]-1'-amino-2',5'-pyrrolidinedione;

8β-morpholino-carbonyl-4bα,8α-dimethyl-12-isopropyl-1β,2β,3β,4,4aβ,4bα,5,6,7,8,8aβ,9,10,10a-tetradecahydro-3,10a-ethenophenanthro[1,2-c]-1'-(2-hydroxyethyl)-2',5'-pyrrolidinedione;

8β-(4-methylpiperazin-1-yl-carbonyl)-4bα,8α-dimethyl-12isopropyl-1β,2β,3β,4,4aβ,4bα,5,6,7,8-,8aβ,9,10,10a-tetradecahydro-3,10a-ethenophenanthro[1,2-c]-1'-amino-2',5'-pyrrolidinedione; and 8β-morpholino-carbonyl-4bα,8α-dimethyl-12-isopropyl-1β,2β,3β,4,4aβ,4bα,5,6,7,8,8aβ,9,10,10a-tetradecahydro-3,10a-ethenophenanthro[1,2-c]-1'-(3,3-dimethylaminopropyl)-2',5'-pyrrolidinedione.

5. The compound of claim 1 which is 8β-morpholino-carbonyl-4bα,8α-dimethyl-12-isopropyl-1β,2β,3β,4,4aβ,4bα,5,6,7,8,8aβ,9,10,10a-tetradecahydro-3,10-a-ethenophenanthro[1,2-c]-1'-(2-hydroxyethyl)-2',5'-pyrrolidinedione.

* * * * *

UNITED STATES PATENT OFFICE
CERTIFICATE OF CORRECTION

Patent No. 3,998,823     Dated December 21, 1976

Inventor(s) John B. Taylor, et al.

It is certified that error appears in the above-identified patent and that said Letters Patent are hereby corrected as shown below:

The formula in the Abstract:

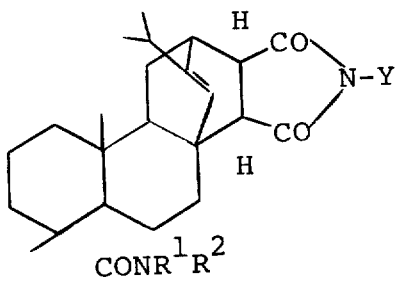      Should Read:      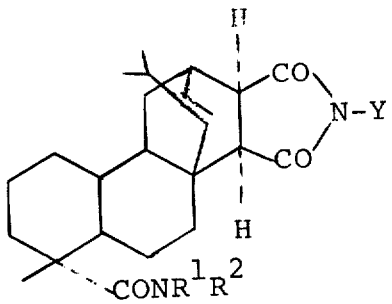

UNITED STATES PATENT OFFICE
CERTIFICATE OF CORRECTION

Patent No. 3,998,823  Dated December 21, 1976

Inventor(s) John Bodenham Taylor et al.

It is certified that error appears in the above-identified patent and that said Letters Patent are hereby corrected as shown below:

Column 1, lines 8-18, the formula:

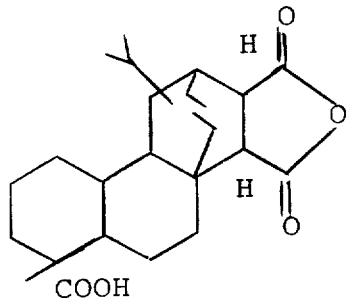   should read:   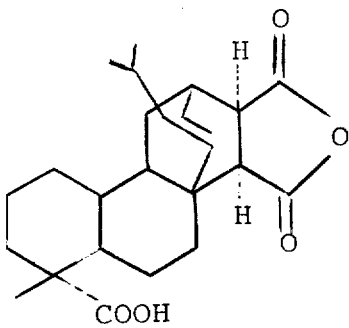

UNITED STATES PATENT OFFICE
CERTIFICATE OF CORRECTION

Patent No. 3,998,823  Dated December 21, 1976

Inventor(s) John Bodenham Taylor et al.

It is certified that error appears in the above-identified patent and that said Letters Patent are hereby corrected as shown below:

Column 1, lines 30-40, the formula:

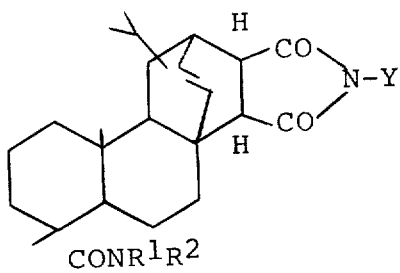 Should Read: 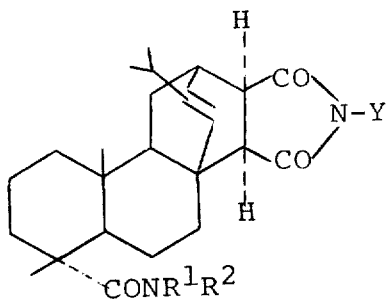

UNITED STATES PATENT OFFICE
CERTIFICATE OF CORRECTION

Patent No.  3,998,823                    Dated  December 21, 1976

Inventor(s)  John Bodenham Taylor et al.

It is certified that error appears in the above-identified patent and that said Letters Patent are hereby corrected as shown below:

Column 2, lines 12-20, the formula I(a):

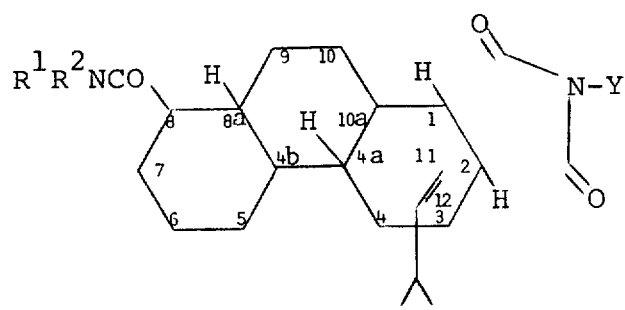

SHOULD READ:

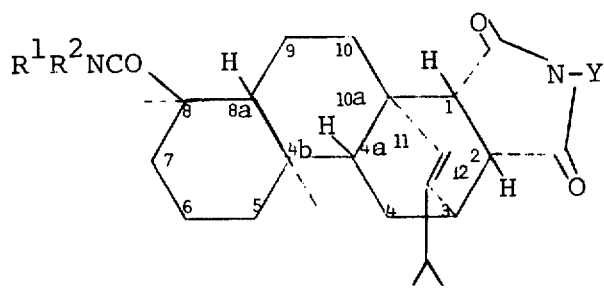

Signed and Sealed this

Ninth Day of May 1978

[SEAL]

Attest:

RUTH C. MASON
Attesting Officer

LUTRELLE F. PARKER
Acting Commissioner of Patents and Trademarks